United States Patent [19]
Steer et al.

[11] Patent Number: 5,830,200
[45] Date of Patent: Nov. 3, 1998

[54] OSTOMY COUPLING

[75] Inventors: Peter L. Steer; Keith G. M. Hollands, both of Sussex; Graham Emery Steer, London; Ronald A. Plass, West Sussex; Howard Barratt, Surrey, all of England

[73] Assignee: E. R. Squibb & Sons, Inc., Princeton, N.J.

[21] Appl. No.: 631,502

[22] Filed: Apr. 12, 1996

[30] Foreign Application Priority Data

Apr. 13, 1995 [GB] United Kingdom .................. 9507666

[51] Int. Cl.$^6$ ........................................................ A61F 5/44
[52] U.S. Cl. ........................ 604/338; 604/342; 604/332; 215/274
[58] Field of Search ..................................... 604/332, 338, 604/334, 342–344; 215/274, 279, 280, 286

[56] References Cited

U.S. PATENT DOCUMENTS 1,562,102  11/1925  Massena ................................. 215/275
5,364,379  11/1994  Ozenne et al. .......................... 604/342

FOREIGN PATENT DOCUMENTS

0572378B1  12/1993  European Pat. Off. ................ 604/338

*Primary Examiner*—Robert A. Clarke
*Attorney, Agent, or Firm*—Stuart E. Krieger

[57] ABSTRACT

It would be desirable to have improved designs of ostomy couplings which embody a springy or resilient split ring as a locking ring.

In an ostomy coupling, first and second coupling members 50, 60 are held together by a springy flexible split locking ring 70. A plurality of tabs 71 symmetrically arranged on each limb of the locking ring 70, can be withdrawn generally radially outwardly by an upward pull on the locking ring to permit separation of the two coupling members. The ring 70 is generally circular in its unstressed condition.

4 Claims, 2 Drawing Sheets

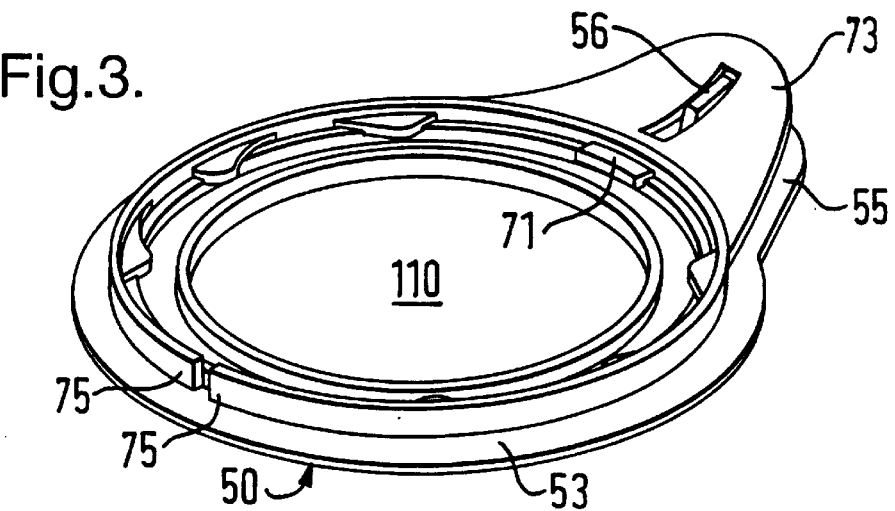
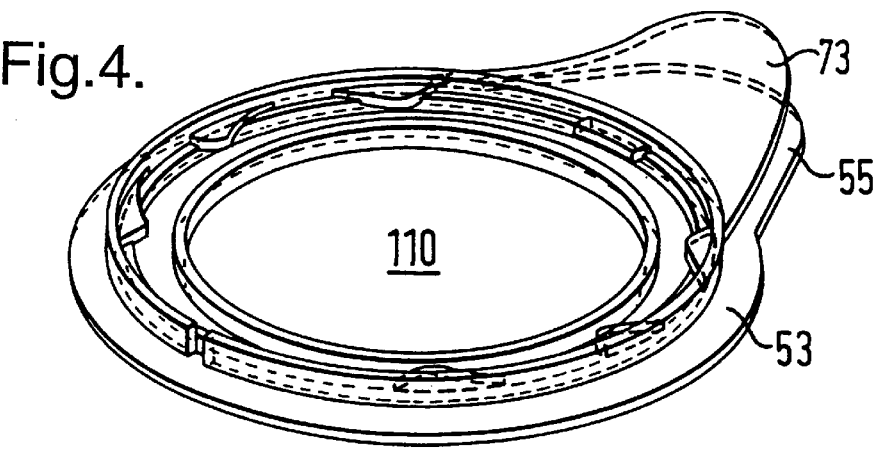
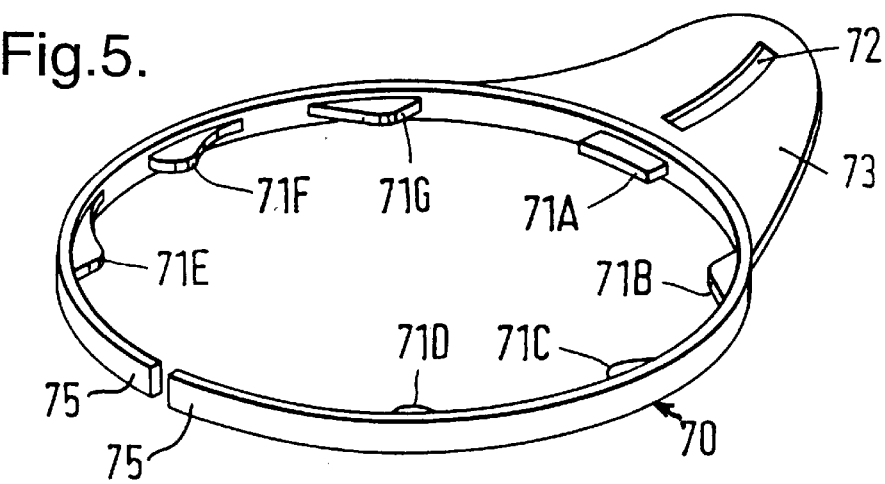

OSTOMY COUPLING

BACKGROUND OF THE INVENTION

This invention relates to an ostomy coupling.

Ostomy couplings are used to connect and disconnect a bag for receiving a stomal discharge to and from a medical grade adhesive pad which is applied to the peristomal area of the skin of the wearer. Many designs of ostomy coupling are known. One which has enjoyed considerable commercial success is described and claimed in U.K. Patent No. 1,571, 657.

A two-part ostomy coupling in which unlocking of two coupling parts is achieved by deforming a ring is disclosed in our U.K. Patent Application No. 9409037.0, filed 6 May 1994, but published after the filing of this application.

An ostomy appliance in which a V-section ring holds coupling members together is disclosed in U.S. Pat. Nos. 5,322,522 and 5,322,523.

In PCT Application WO91/01119, published 1991 and corresponding to European Patent 482 104B, there is disclosed a locking ring for an ostomy coupling. An ostomy coupling which embodies such a ring is shown in European Patent 572 378B. Features of this design are that inwardly sprung tongues on the ring peripherally surround the joined coupling parts and that a press-button engagement device as well as a hook and detent engagement device are included, apparently in a quest for secure retention of the locking ring on the coupling parts. It appears inevitable that quite intricate manipulation of this design of coupling is needed when applying or removing the bag.

It has been proposed by Kubo, in Japanese Utility Model No. 62-11610, published Feb. 1985, that an ostomy device should have a double female ring structure which can interengage with a male ring. The male ring may be on the bag and the female ring on a skin-attachable adhesive pad, or vice-versa. The outer ring on the female ring is circular and flexible and has a pair of inwardly-extending catches at opposite ends of a diameter. By pressing on two diametrically extending lugs, whose diameter is substantially at right angles to the diameter joining the catches, the outer female ring is deformed so that the catches are caused to move radially outwardly, so permitting separation of the two coupling parts.

This arrangement, though perhaps operable in theory, has serious disadvantages in practice, for example (i) to connect or disconnect it is necessary to hold the coupling at four places, approximately spaced at 90° intervals around the periphery, (ii) pressing on two diametrically opposed regions will tend to bend the coupling out of its normal plane and the forces applied may easily cause the body side pad to be partially (or wholly) detached from the skin of the wearer, also the need to press in both ends of the diameter fully, and simultaneously, means that releasing the bag-side coupling is subject to uncertainty, (iii) the repeated attachment and withdrawal of the bag-side coupling part will cause the o-ring (provided to prevent escape of excreted matter between the male and female rings) to become worn, so compromising its sealing qualities with potentially highly embarrassing and undesirable results, (iv) the wearer may find it difficult to determine whether or not the two coupling parts are properly engaged, (v) the accuracy and forces needed for manipulation to connect or disconnect will be well beyond the capability of an infirm, confused, elderly or impatient wearer; (vi) it is hard to be sure that the appliance is properly locked; and (vii) in the case of large sizes, the old and infirm will find it physically difficult to span with their hand and push in diametrally opposed regions of the ring. A further disadvantage of Kubo and of many present day ostomy couplings is that they extend outwardly from the body an undesirable distance giving rise to embarrassing bulges under clothing.

SUMMARY OF THE INVENTION

It is an aim of this invention to provide an improved design.

According to the present invention, there is provided a coupling including a first coupling member and a second coupling member which are mutually interengageable and which surround an orifice, the coupling also including a resilient split ring which encircles the two coupling members and has a handle member arranged for upward movement when manipulated by the wearer to cause the split ring to be deformed such that radially-inwardly extending tabs on the ring are shifted between respective first positions in which the split ring is undeformed and the tabs lock the two coupling members together and respective second positions in which the split ring is deformed in such a way as to shift the tabs outwardly to positions where they permit separation of the two coupling parts.

According to a preferred embodiment of the invention, the tabs are symmetrically arranged on the ring, and the split ring is made of a springy flexible plastics material. An acetal resin is preferred.

BRIEF DESCRIPTION OF THE DRAWING

The invention will be better understood from the following non-limiting description of an example thereof given with reference to the accompanying drawings in which:

FIG. 3 is a perspective view of what is shown in FIG. 1;

FIG. 4 is a view similar to FIG. 3 showing the first coupling member but not showing the second coupling member; and FIG. 5 is a perspective view of a locking ring usable in this invention.

DETAILED DESCRIPTION OF THE INVENTION

The ostomy coupling illustrated in FIGS. 1–5 comprises first and second coupling members 50 and 60 and a split locking ring 70. The first coupling member may be a plastics moulding and may be made of low density polyethylene. The second coupling member may also be a plastics moulding, e.g. of EVA. The first and second couplings may be respectively bag-side and body-side, or vice versa.

For the material of the locking ring 70, good results have been achieved with an acetal copolymer known as 'KEMATAL' (Registered Trade Mark) which is also referred to as polyoxymethylene (POM) and is available from Hoechst. This is crystalline thermoplastic with an exceptionally stable polymer structure; a suitable grade is 'HOSTAFORM' (Registered Trade Mark) C. 27021.

Figure 1:
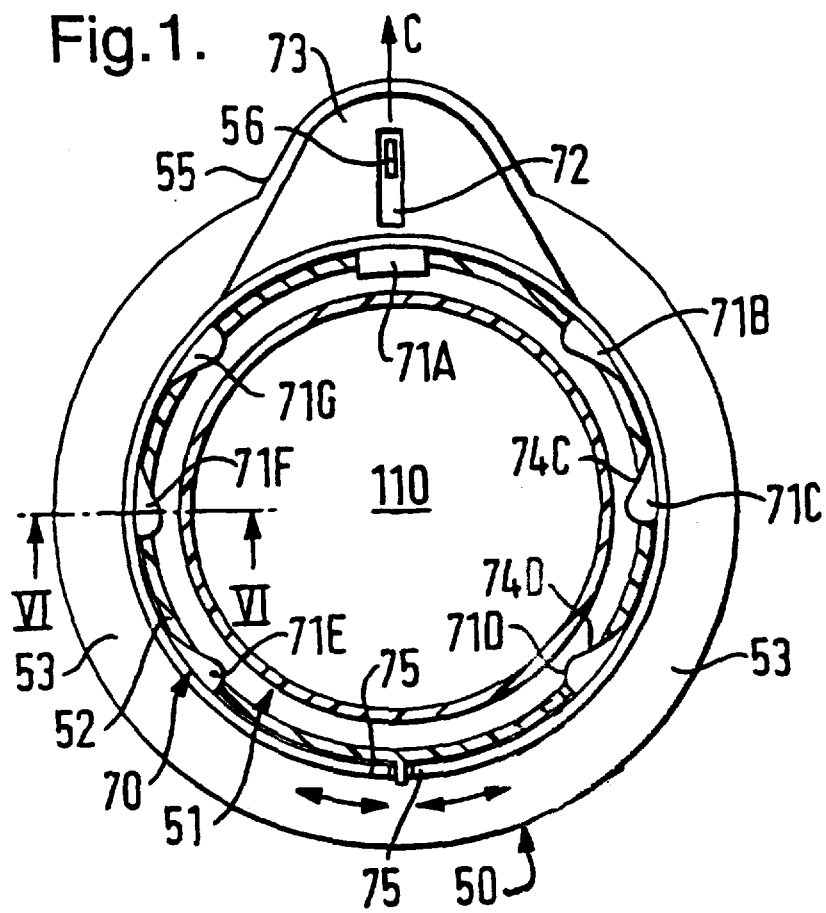
FIG. 1 is a plan view of an embodiment of the invention, showing part of the first coupling member and the locking ring.
Figure 2:
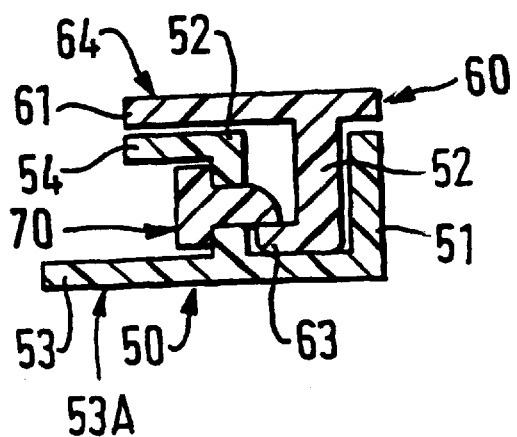
FIG. 2 is a cross-sectional view on the plane VI-VI in FIG. 1, but also showing the part at one end of a diameter, of a second coupling member, and illustrating the locking function of tabs on the locking ring.

As mentioned, the ostomy coupling includes a first coupling member 50, a second coupling member 60, seen only in FIG. 2, and a split locking ring 70. It will be realised that the second coupling member is circular or closed loop shape, so as to be complementary to the ring and the first coupling member. FIG. 2 illustrates one end of a diameter. The first coupling member has an inner wall 51, an outer wall 52, apertures in that wall 52 and a flange 53 attached to a medical grade adhesive pad (not shown). A cover flange 54 assists in retaining the split ring 70 in position in the coupling, and a guidance stud 56 projects upwardly from the surface of the flange 53 and extends into an elongate slot 72, to be later described.

The second coupling member 60 has a flange 61 to the exposed surface 64 of which a wall of an ostomy pouch, not shown, is attached. The second coupling member has an encircling wall 62 and a radially outwardly extending rim 63 over which tabs 70 engage. This engagement provides the coupled condition of the coupling, illustrated in FIG. 2.

A split locking ring is embodied in this coupling, and is seen best in FIG. 5. It comprises locking tabs 71A–G, a gripping tab 73, and a slot 72 in that tab. The slot 72 is not shown in FIG. 4. The free ends of the locking ring are shown at 75. As seen in plan, the locking tab 71A is generally rectangular, but the remaining tabs 71B–71G are approximately half-pear-shaped. Each of these tabs has a curved surface, e.g. 74C, 74D, FIG. 1. These surfaces are provided so that approximately radially outward movement of the locking tabs is caused when the gripping tab 73 is pulled vertically upwards as indicated by the arrow C. The presence of the stud 56 extending into the slot 72 ensures that a substantially linear movement radially outwardly, i.e. upwardly in normal use, of the split locking ring is maintained. Of course as will be understood, upon this upward movement taking place, the free ends 75 of the locking ring move apart as sloped or curved surfaces 74 on the tabs 71 cause the tabs to move outwardly and thus release the rim 63. Hence the bag-side coupling member 60 and the bag attached thereto can be readily separated from the first coupling member 50 by pulling in an outward axial direction of the coupling. A medical grade adhesive pad is attached to the lower (as seen in FIG. 2) surface 53A of the flange 53 so that the appliance can be attached to the wearer.

The medical grade adhesive pad may comprise a base which is preferably a thin film of polymeric material such as polyethylene and an adhesive layer situated on the rear surface of a base. Such an adhesive layer is preferably formed as a homogeneous blend of one or more pressure-sensitive viscous or elastomeric materials having intermittently dispersed therein one or more water-soluble or swellable hydrocolloid gums and may also include one or more thermoplastic elastomers and/or one or more swellable cohesive strengthening agents.

It will be understood that modifications, alterations, and improvements could be made to the invention. For example, instead of having coupling members which are circular, it would be possible for them to be oval or of other closed loop shape. While the preferred material for the locking ring in each embodiment is an acetal resin, other plastics materials having the appropriate flexible and springy characteristics could be employed. Other specific mechanisms could be employed to achieve outward springing of the split locking ring thereby permitting the coupling parts to be separated. A flexible deflectible sealing strip may be provided on either the coupling member 50 or 60 to reduce the possibility of leakage and to take up any tolerances between the coupling members which may arise in manufacture.

What is claimed is:

1. An ostomy coupling comprising;

first and second coupling members capable of being coupled together, each of said members having a central stomal opening, said first coupling member having a flange with a projection receiving channel, said channel being defined at least in part by a concentric inner and outer wall, said inner wall being positioned closer to said stomal opening, said outer wall having a plurality of tab-receiving slots extending therethrough, said second coupling member having a projection receivable in said channel when said first and second members are properly pushed together, said projection being lockable in said channel, and a resilient, circular releasably lockable locking ring positionable circumferentially about said outer wall, said locking ring including a plurality of tabs projecting radially inwardly through said slots so as to lock said projections in said channel which said coupling members are coupled together, said locking ring including a manually grippable portion, said grippable portion being movable radially outwardly so as to move said locking ring radially outwardly and withdraw said tabs from said slots of said locking ring releasing said projection, said locking resiliently returning to lock said projections in said channel upon release of said grippable portion when said coupling members are coupled together.

2. The ostomy coupling according to claim 1 wherein said locking ring is made of acetal resin.

3. The ostomy coupling according to claim 1 further comprising a medical grade adhesive pad attached to the body side coupling member, said pad comprising a base which is a thin film of polymeric material such as polyethylene and an adhesive layer situated on the rear surface of the base, said adhesive layer formed either as a homogeneous blend of one or more pressure-sensitive viscous or elastomeric materials having intermittently dispersed therein one or more water-soluble or swellable hydrocolloid gums, or by one or more thermoplastic elastomers and/or one or more swellable cohesive strengthening agents.

4. The ostomy coupling according to claim 1 wherein said grippable portion includes a slot and a coupling member has a stud positionable in said slot, said stud being guided in its movement in said slot so as to constrain said radially outward movement of said locking ring.

* * * * *